US00PP27557P2

(12) United States Plant Patent
Verschoor

(10) Patent No.: US PP27,557 P2
(45) Date of Patent: Jan. 17, 2017

(54) ***PHLOX* PLANT NAMED 'VERSDE'**

(50) Latin Name: *Phlox paniculata*
Varietal Denomination: Versde

(71) Applicant: Janus Verschoor, Haarlem (NL)

(72) Inventor: Janus Verschoor, Haarlem (NL)

(73) Assignee: A. VERSCHOOR HORTICULTURE IMPORT-EXPORT B.V., Haarlem (NL)

( * ) Notice: Subject to any disclaimer, the term of this patent is extended or adjusted under 35 U.S.C. 154(b) by 0 days.

(21) Appl. No.: 14/756,963

(22) Filed: Nov. 2, 2015

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — Penny J. Aguirre

(57) ABSTRACT

A new cultivar of *Phlox*, 'Versde', characterized by its very dwarf and compact plant habit, its dark pink flowers, its dark green, shiny foliage, its vigorous growth habit, its strong basal branching, and its low susceptibility to powdery mildew.

2 Drawing Sheets

Botanical classification: *Phlox paniculata.*
Cultivar designation: 'Versde'.

BACKGROUND OF THE INVENTION

The present invention relates to a new and distinct cultivar of *Phlox* plant, botanically known as *Phlox paniculata* 'Versde' and will be referred to hereafter by its cultivar name, 'Versde'. The new cultivar represents a new herbaceous perennial grown for landscape use.

The Inventor discovered 'Versde' in a field in Haarlem, The Netherlands in August of 2011 as a chance seedling. The probable parentage of 'Versde' is an open pollinated plant of *Phlox paniculata* 'Younique Purple' (not patented) as the field had been planted with plants of 'Younique Purple'.

Asexual propagation of the new cultivar was first accomplished by stem cuttings in Haarlem, The Netherlands in fall of 2011 by the Inventor. Asexual propagation by stem cuttings, root cuttings, and tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Versde' as a unique cultivar of *Phlox*.

1. 'Versde' exhibits a very dwarf and compact plant habit.
2. 'Versde' exhibits dark pink flowers.
3. 'Versde' exhibits dark green, shiny foliage.
4. 'Versde' exhibits a vigorous growth habit.
5. 'Versde' exhibits strong basal branching.
6. 'Versde' exhibits some resistance to powdery mildew.

The female parent of 'Versde', 'Younique Purple', differs from 'Versde' in bring taller in height, in having less basal branching, and in having flowers that are brighter pink in color. 'Versde' can be compared to the cultivars 'Purple Paradise' (not patented) and 'Purple Kiss' (U.S. Plant Pat. No. 19,514). Both are similar to 'Versde' in having a vigorous growth habit and in having some resistance to powdery mildew. 'Purple Paradise' differs from 'Versde' in having stems that are longer in length, in having flowers that are more purple in color, and in having less basal branching. 'Purple Kiss' differs from 'Versde' in having stems that are longer in length, in having flowers that are purple in color with a white eye, in having less basal branching, and in commencing bloom later.

BRIEF DESCRIPTION OF THE DRAWINGS

The accompanying colored photographs illustrate the overall appearance and distinct characteristics of the new *Phlox*. The photographs were taken of an 18 month-old plant (from an unrooted cutting) of 'Versde' as field grown in Haarlem, The Netherlands and placed in a container for the photographs.

The photograph in FIG. 1 is a view of a plant of 'Versde' in bloom.

Figure 1:
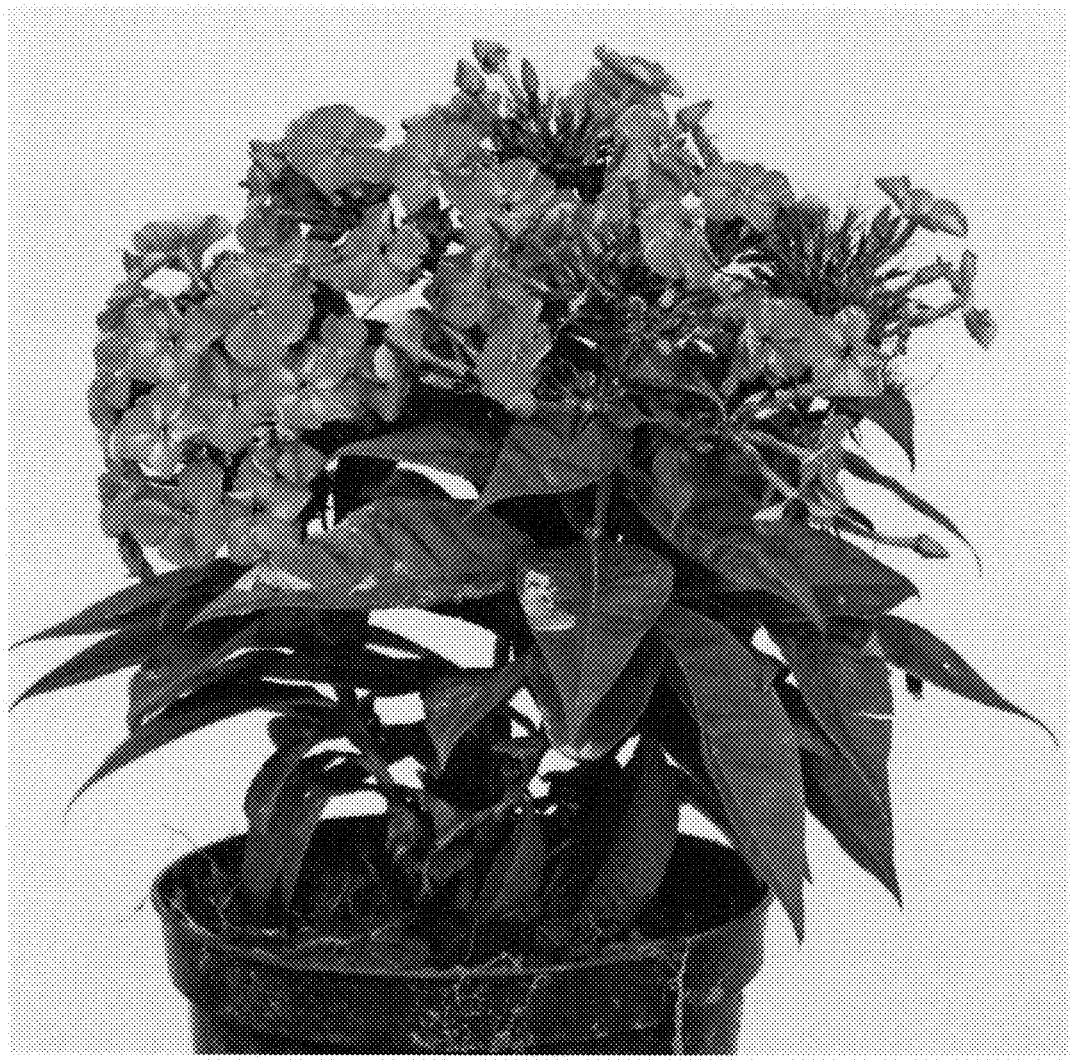
Figure 2:
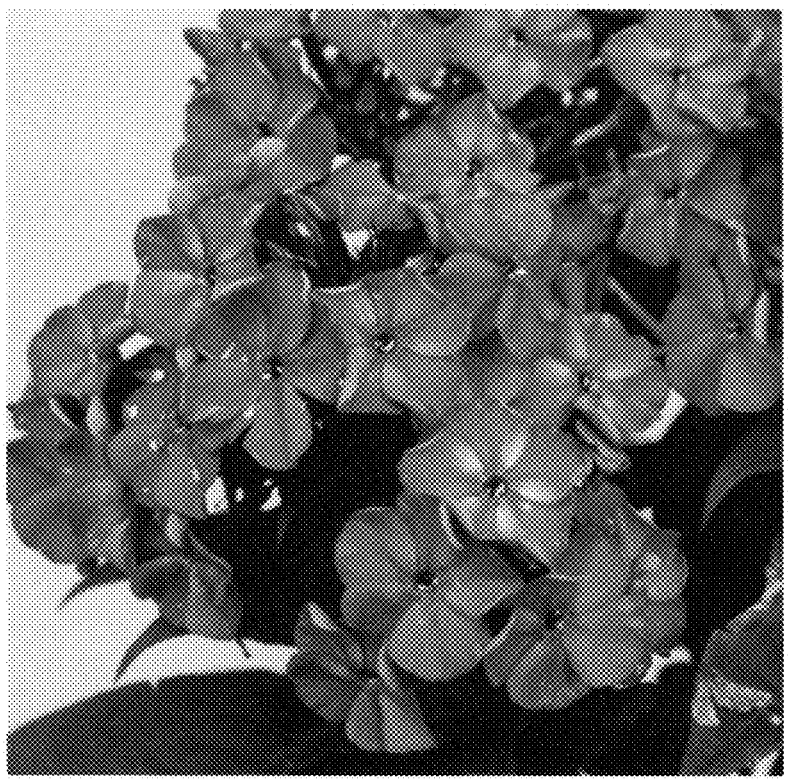

The photograph in FIG. 2 is a close-up view of an inflorescence of 'Versde'.

Figure 3:
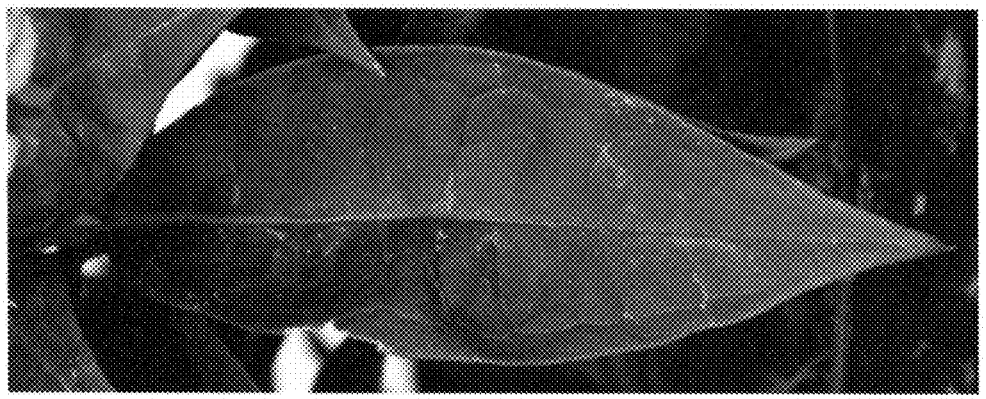

The Photograph in FIG. 3 provides a close-up view of a leaf of 'Versde'.

The colors in the photographs may differ slightly from the color values cited in the detailed botanical description, which accurately describe the colors of the new *Phlox*.

DETAILED BOTANICAL DESCRIPTION OF THE PLANT

The following is a detailed description of 18 month-old plants (from an unrooted cutting) of the new cultivar as field grown in Haarlem, The Netherlands. The plants were grown under average day temperatures of 14° C. to 25° C. and average night temperatures of 4° C. to 18° C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Mid June to September in the Netherlands.

*Plant type*.—Herbaceous perennial.

*Plant habit*.—Very dwarf and compact.

*Height and spread*.—Reaches an average of 30 cm in height and about 40 cm in spread.

*Hardiness*.—At least in U.S.D.A. Zones 4 to 9.

*Diseases*.—Has shown some resistance (less susceptibility when grown under the same circumstances as other cultivars) to powdery mildew caused by *Erysiphe cichoracea*.

*Root description*.—Fibrous.

*Growth rate*.—Vigorous.

*Propagation*.—Stem cuttings, root cuttings, and tissue culture.

*Root initiation*.—About 30 days in summer.

*Root development*.—About 26 weeks from a rooted cutting to fully develop in a 1.5 liter container.

Stem description:

*Stem quantity*.—Average of 4 flowering stems.

*Stem size*.—15.3 cm in length (excluding inflorescence), average of 3.5 mm in diameter.

*Stem shape*.—Nearly round, slightly angled.

*Stem strength*.—Strong.

*Stem color*.—Between 144A and 144B.

*Stem surface*.—Glabrous and moderately glossy.

*Stem aspect*.—Held in an average angle of 55° to soil level (=0°).

*Internode length*.—An average of 1.5 cm.

*Branching habit*.—Basal flowering stems, well-branched.

Foliage description:

*Leaf shape*.—Narrow ovate to elliptic, moderately carinate.

*Leaf division*.—Simple.

*Leaf base*.—Truncate.

*Leaf apex*.—Long apiculate.

*Leaf venation*.—Pinnate, upper side 144A, lower side 144B.

*Leaf margins*.—Entire, very slightly revolute.

*Leaf attachment*.—Petiolate.

*Leaf arrangement*.—Opposite.

*Leaf surface*.—Very slightly rugose, both sides very slightly glossy.

*Leaf color*.—Young upper surface; 143A, young lower surface; 143B, mature upper surface; NN137A, mature lower surface; 147B.

*Leaf size*.—An average of 10.9 cm in length and 4.1 cm in width.

*Leaf quantity*.—An average of 22 (11 pairs).

*Petioles*.—V-shaped, an average of 2.5 mm in height, 3 mm in width and 3.5 mm in length, both surfaces 144B in color, upper side tinged between N187A and N187B, glabrous surface.

Flower description:

*Inflorescence type*.—Compound terminal panicle.

*Lastingness of inflorescence*.—About 3 to 4 weeks from the opening of the first flower to senescence of last flower per inflorescence, individual flower lasts about 10 days, inflorescences are continuously produced during the bloom season.

*Inflorescence size*.—An average of 9.8 cm in height and 13.4 cm in width.

*Flower fragrance*.—Moderate, sweet and pleasant *phlox* fragrance.

*Flower number*.—Average of 90 per inflorescence.

*Flower aspect*.—Upright to outward.

*Flower bud*.—An average of 2.3 cm in length and up to 4.5 mm in width, narrow oblanceolate in shape, color; 77A, immature calyx N79B, glabrous surface.

*Flower form*.—Explanate with tubular base.

*Flower size*.—An average of 3.4 cm in diameter and 2.5 cm in depth.

*Petals*.—5, self-cleaning, surfaces glabrous, upper surface matte, lower side slightly glossy, rotate and overlapping arrangement, petals are fused 55% into tube, spathulate in shape, margins entire, apex rounded to slightly retuse, average of 3.4 cm in length (lower 1.9 cm fused into tube), average of 1.8 cm in width, color when opening upper side; N74A, tube N79C, color when opening lower side; 70A to 72B, tube N79C, color fully open upper side; N74A, tube N79C, color fully open lower side; 72B, N79B to N79C.

*Calyx*.—Campanulate in form, an average of 1.2 cm in length and 5 mm in width.

*Sepals*.—5, base lower 16% fused, linear in shape, margins entire, apex narrowly apiculate, an average of 1.2 cm in length and 1.75 mm in width, surface is glabrous and very slightly glossy, color; immature upper surface N144D, main vein and margins strongly tinged N187A, immature lower surface 143C, main vein and margins strongly tinged N187A, mature upper surface N144D, main vein and margins strongly tinged N187A, mature lower surface 143C, main vein and margins strongly tinged N187A.

*Peduncles*.—Oval in shape, strong, primary an average of 5.9 cm in length and 3 mm in width, secondary an average of 3.8 cm in length and 1.5 mm in width, primary held upright, secondary held at about a 45° angle, glabrous surface, color 144C.

*Pedicels*.—Oval in shape, strong, an average of 7 mm in length and 1 mm in width, glabrous surface, held at an average angle of 40° (0°=straight on top of peduncle), color 143C.

Reproductive organs:

*Gynoecium*.—Pistil; 1, 1.7 cm in length, stigma; cleft (3-parted), 150C in color, style; 1.6 cm in length, N77D in color, ovary; superior and 143A to 143B in color.

*Androcoecium*.—5 stamens, anthers; basifixed and oblong in shape, 2 mm in length and 4D in color, filaments; implanted in petal, 0.5 mm in length, 75C to 75D in color, pollen is low in quantity and 11D in color.

*Seeds*.—None observed.

It is claimed:

1. A new and distinct cultivar of *Phlox* plant named 'Versde' as herein illustrated and described.

* * * * *